United States Patent [19]
Gates

[11] Patent Number: 5,522,874
[45] Date of Patent: Jun. 4, 1996

[54] MEDICAL LEAD HAVING SEGMENTED ELECTRODE

[76] Inventor: James T. Gates, 9695 206th Ave. N., Maple Grove, Minn. 55369

[21] Appl. No.: 282,122

[22] Filed: Jul. 28, 1994

[51] Int. Cl.⁶ .................................................. A61N 1/05
[52] U.S. Cl. ............................................. 607/127; 607/120
[58] Field of Search ................................ 607/120–123, 607/125–131; 128/642

[56] References Cited

U.S. PATENT DOCUMENTS

| | | |
|---|---|---|
| 3,476,116 | 11/1969 | Parsonnet et al. . |
| 3,827,428 | 8/1974 | Hon et al. . |
| 3,906,938 | 9/1975 | Fleischhacker . |
| 3,911,928 | 10/1975 | Lagergren . |
| 4,106,512 | 8/1978 | Bisping . |
| 4,146,036 | 3/1979 | Dutcher et al. . |
| 4,217,913 | 8/1980 | Dutcher . |
| 4,236,529 | 12/1980 | Little . |
| 4,311,153 | 1/1982 | Smits . |
| 4,350,169 | 9/1982 | Dutcher et al. . |
| 4,357,946 | 11/1982 | Dutcher et al. . |
| 4,408,604 | 10/1983 | Hirshorn et al. . |
| 4,498,482 | 2/1985 | Williams . |
| 4,628,943 | 12/1996 | Miller ............................ 607/127 |
| 4,649,937 | 3/1987 | DeHaan et al. . |
| 4,760,852 | 8/1988 | Lekholm . |
| 4,784,161 | 11/1988 | Skalsky et al. ................. 607/122 X |
| 4,796,642 | 1/1989 | Harris . |
| 4,815,478 | 3/1989 | Buchbinder et al. . |
| 4,819,661 | 4/1989 | Heil, Jr. et al. . |
| 4,827,940 | 5/1989 | Mayer et al. . |
| 4,844,099 | 7/1989 | Skalsky et al. . |
| 4,917,106 | 4/1990 | Olivier . |
| 4,953,564 | 9/1990 | Berthelson . |
| 4,972,848 | 11/1990 | Di Domenico et al. . |
| 5,002,067 | 3/1991 | Berthelsen et al. . |
| 5,003,992 | 4/1991 | Holleman et al. . |
| 5,014,720 | 5/1991 | Barcel et al. . |
| 5,052,404 | 10/1991 | Hodgson . |
| 5,165,421 | 11/1992 | Fleischhaker et al. . |
| 5,211,636 | 5/1993 | Mische . |
| 5,213,111 | 5/1993 | Cook et al. . |
| 5,234,451 | 8/1993 | Osypka . |
| 5,246,014 | 9/1993 | Williams et al. . |
| 5,259,394 | 11/1993 | Bens . |
| 5,282,844 | 2/1994 | Stokes et al. ............................ 607/120 |
| 5,324,325 | 6/1994 | Moaddeb ................................ 607/120 |

OTHER PUBLICATIONS

Medtronic Technical Manual, Myocardial, Unipolar Lead, Mar. 1991, UC9001746bEN 195409–002.

*Primary Examiner*—Marvin M. Lateef
*Assistant Examiner*—Jeffrey R. Jastrzab
*Attorney, Agent, or Firm*—Michael J. Jaro; Harold R. Patton

[57] ABSTRACT

A stylet-actuated, steroid-eluting, screw-in, endocardial, transvenous bipolar pacing lead. In an embodiment, the lead is provided, with a sharpened helix. Advancing and retraction of the helix is accomplished with a stylet having a flattened, screw-driver tip. Rotation of the stylet imparts rotation to the helix assembly, causing the helix to advance or retract. A segmented tip electrode having a porous coating thereon allows steroid from a monolithic controlled released device housed within the electrode assembly to be eluted at the location of the implant site.

15 Claims, 6 Drawing Sheets

MEDICAL LEAD HAVING SEGMENTED ELECTRODE

REFERENCE TO RELATED APPLICATION

This application is related to the co-pending U.S. application of James T. Gates and Kenneth B. Stokes entitled "MEDICAL ELECTRICAL LEAD SYSTEM HAVING A TORQUE TRANSFER STYLET" Ser. No. 08/282,421 filed this same day and assigned to the assignee of the present invention.

FIELD OF THE INVENTION

This invention relates to the field of body-implantable medical device systems, and in particular to a body-implantable medical device system which includes a medical electrical lead having a segmented electrode.

BACKGROUND OF THE INVENTION

In the medical field, various types of body-implantable leads are known and used. Cardiac pulse generators, in particular, use implanted leads to both sense cardiac function and deliver stimulation pulses. One type of commonly used implantable lead is an endocardial lead.

Endocardial leads are attached at their proximal end to an implantable pulse generator and at their distal end to the endocardium of a cardiac chamber. Often the lead assembly is inserted into the heart through a vein. The lead generally has an inner conductor covered by an insulative sheath.

The distal end of an endocardial lead may engage the endocardium by either an active fixation mechanism or a passive fixation mechanism. Passive fixation mechanisms, such as a time assembly, lodge or passively fix the lead to the heart. Active fixation mechanisms use a structure, such as a helix or hook, to engage into or actively fix themselves to the heart.

A sharpened helix has been found to provide a reasonably secure means for fixing the lead to the heart. An exposed sharpened helix may damage a vein, however, during introduction. Thus many active fixation leads have helixes which either retract into the lead body or are shielded during introduction. See for example, U.S. Pat. No. 4,972,848 of Di Domenico (helix shielded within lead body which may be extended to engage cardiac tissue); U.S. Pat. No. 5,003,992 of Holleman et al. (plunger through helix guards against damage to tissue by the helix and may be retracted to engage cardiac tissue) and U.S. Pat. No. 4,827,940 of Mayer et al. (soluble cover shields helix until positioned proximate fixation site.) Among the most preferred methods of shielding a helix is where the helix may be retracted within or extended from the lead body.

While preventing the helix from unintentionally engaging tissue is important, the helix itself cannot be too small. Specifically if the helix is too small it will not truly screw through tissue, but rather will only drill or stick into tissue like a needle, providing very little fixation. Thus the helix must be of a certain minimal diameter. Because the helix preferably is retractable within the lead body, the lead body distal end must also be of a certain minimal size.

Besides having the helix at the distal end, it is generally preferable to also locate an electrode at the distal end of the lead. In the design where the helix may retract within the lead body, a distal tip electrode permit cardiac sensing without having to first screw the helix into the tissue. Generally, however, it is preferable to minimize the surface area of the electrode. A small surface area increases the impedance of the electrode. This, in turn, reduces the current required for stimulating pulses. Smaller surface areas, however, may inhibit cardiac sensing. In addition, it is also often desirable to provide the capability for the electrode to deliver a drug (such as asteroid) in the vicinity of the electrode/tissue interface.

In short an active fixation lead has a variety of components having competing requirements. The distal end should not be too small so as to accommodate the helix, yet the electrode located at the distal end should not be too large. In addition is also preferable for the electrode to deliver a drug, such as asteroid.

SUMMARY OF THE INVENTION

Thus it is an object of the present invention to provide an active fixation lead which will permit a fixation helix to be retracted within or extended from the lead body.

It is a further object of the present invention to provide an active fixation lead which provides a suitably dimensioned electrode at the distal end.

It is a further object of the present invention to provide an active fixation lead which provides an electrode which contact the heart which may elute a drug, such as asteroid.

The present invention is directed to an active-fixation transvenous lead. In one embodiment, the distal end of the lead contains a capsule which houses a helical fixation screw molded into a plastic stylet socket. The helical screw passes through a similarly helical channel in a molded sealing cap by means of force applied with a stylet equipped with a slotted head or screw-driver blade. Rotation of the stylet extends or retracts the helix from the sealing cap and thus from the lead body.

Further in accordance with the disclosed embodiment of the invention, an electrode is provide a the distal end of the lead, the electrode comprising a segmented pattern of electrically common tabs having holes arranged radially about the distal tip of the lead. Each of the tabs has an approximate geometric surface area of 0.5-mm$^2$. A porous structure is sintered over the tabs. Asteroid monolithic controlled release device (MCRD) is located in a void immediately proximal to the cathode.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein:

FIG. 2b is a greatly enlarged side cross-sectional view of a distal portion of the electrode assembly of FIG. 2a;

FIG. 2c is a greatly enlarged side cross-sectional view of a proximal portion of the electrode assembly of FIG. 2a;

FIGS. 3a and 3b are front and cross-sectional side views, respectively, of a distal tip electrode in the electrode assembly of FIG, 2a;

FIG. 5 is a side view of a helix assembly from the electrode assembly of FIG. 2a;

FIGS. 6a and 6b are rear and cross-sectional side views, respectively, of a helix seal in the electrode assembly of FIG. 2a.

DETAILED DESCRIPTION OF THE INVENTION

The present invention is described within the context of a screw-in bipolar transvenous endocardial lead adapted for use in connection with an implantable cardiac pulse generator, such as the Medtronic Legend™ or other models commercially available from Medtronic, Inc., Minneapolis, Minn. The present invention, however, may be advantageously practiced in conjunction with many different types of implantable medical devices as well as many other various embodiments of a medical electrical lead besides the particular bipolar lead described herein.

Figure 1:
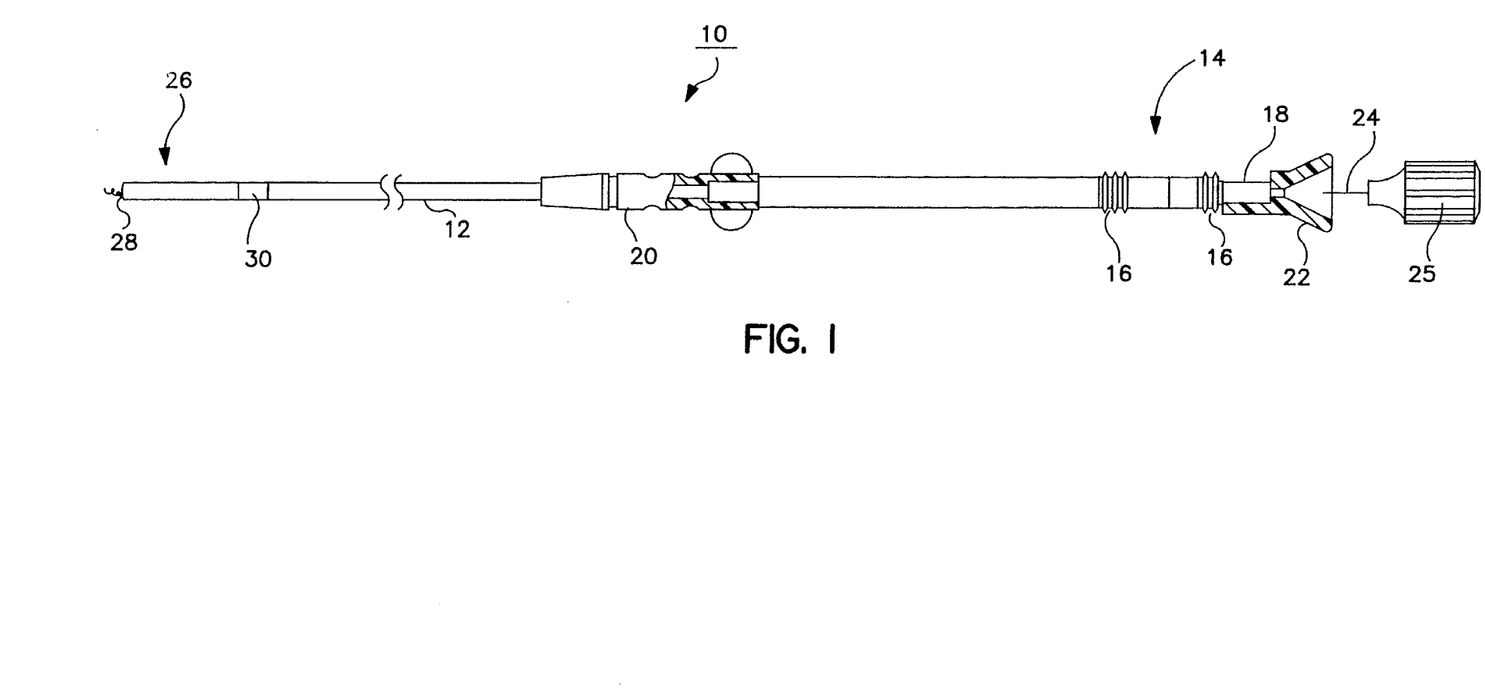
FIG. 1 is a plan view of a stylet-actuated, steroid-eluting, bipolar transvenous pacing lead in accordance with one embodiment of the invention.

Referring to FIG. 1, there is a plan view of a stylet-activated, steroid eluting, screw-in endocardial bipolar pacing lead 10 having a flexible, elongate lead body 12 covered by an insulative sleeve, such as polyurethane or silicone rubber. Terminal assembly 14 is provided at the proximal end for coupling lead 10 to an implantable pulse generator (not shown.) Terminal assembly 14 has sealing rings 16 and terminal pin 18, all of a type known in the art.

An anchoring sleeve 20 (shown partially in cross-section) may also be provided for suturing lead body 12 to body tissue. Anchoring sleeve 20 and terminal assembly 14 are preferably fabricated from silicone rubber, although they may also be constructed of any other suitable biocompatible material known in the art.

Lead 10 may also include stylet guide 22 and stylet assembly 24 coupled to terminal pin 18 for imparting stiffness to lead 10 during placement and for actuation of the lead's fixation helix, described below. Stylet guide 22 and stylet assembly 24 are typically discarded after use and before connection of terminal pin 18 to a pacemaker pulse generator.

With continued reference to FIG. 1, an electrode and fixation assembly designated generally as 26 is disposed at the distal end of lead body 12. Electrode and fixation assembly 26 is, in the disclosed embodiment, of the bipolar type and has tip electrode 28 at its distal end and a ring electrode 30 spaced proximally back from the distal end. As will be appreciated by those of ordinary skill in the art, tip electrode 28 and ring electrode 30 are coupled to separate, insulated lead conductors (not shown in FIG. 1) which extend along the length of lead body 12. Lead conductors are preferably configured as concentric multi-filar coils of a platinum-iridium alloy or any other suitable alloy, such as MP35N. This configuration allows for a longitudinal lumen to exist along the length of lead body 12, such that a stylet may be received therein.

Figure 2A:
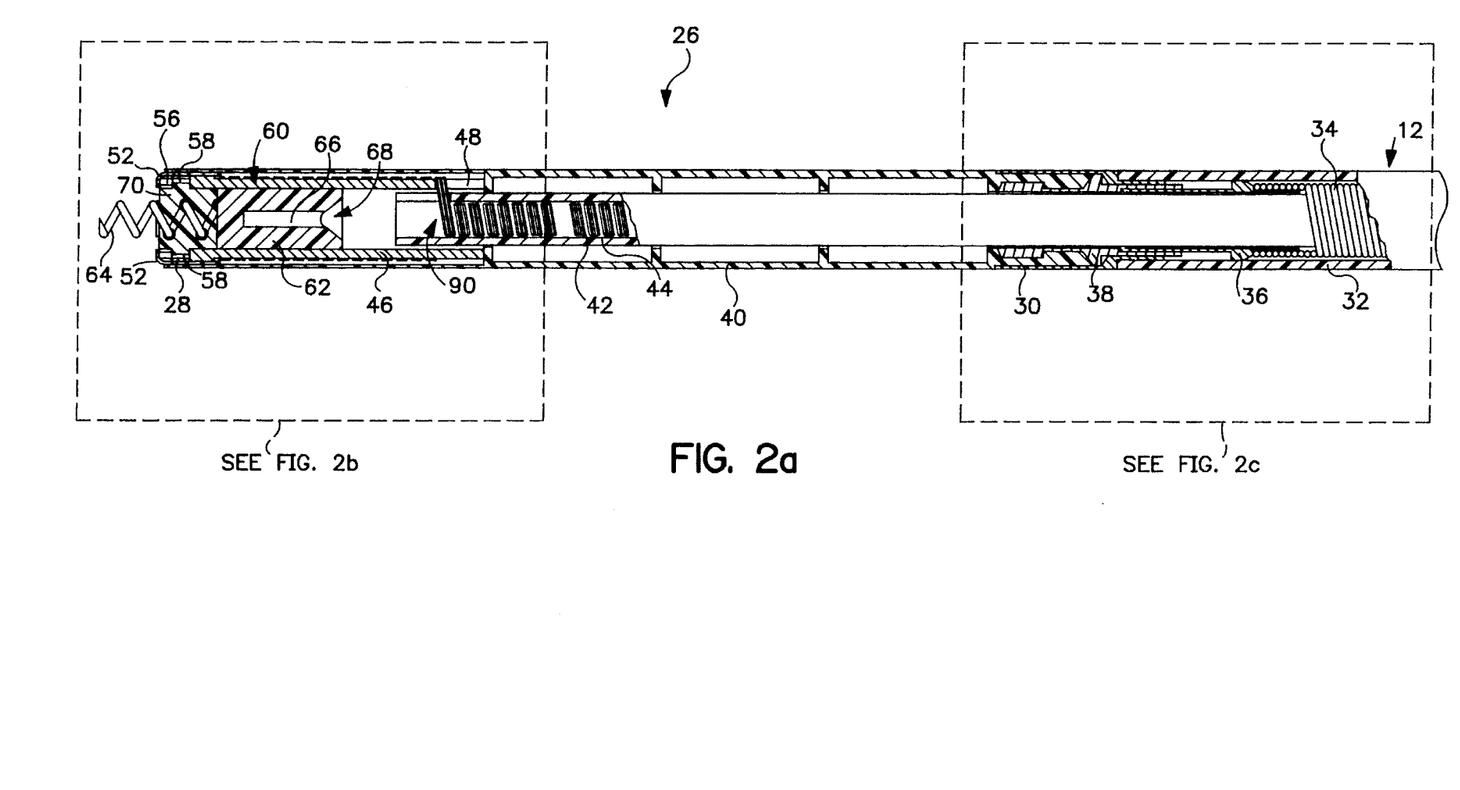
FIG. 2a is a greatly enlarged side cross-sectional view of a distal segment of the lead of FIG. 1 including the lead's electrode assembly.
Figure 2B:
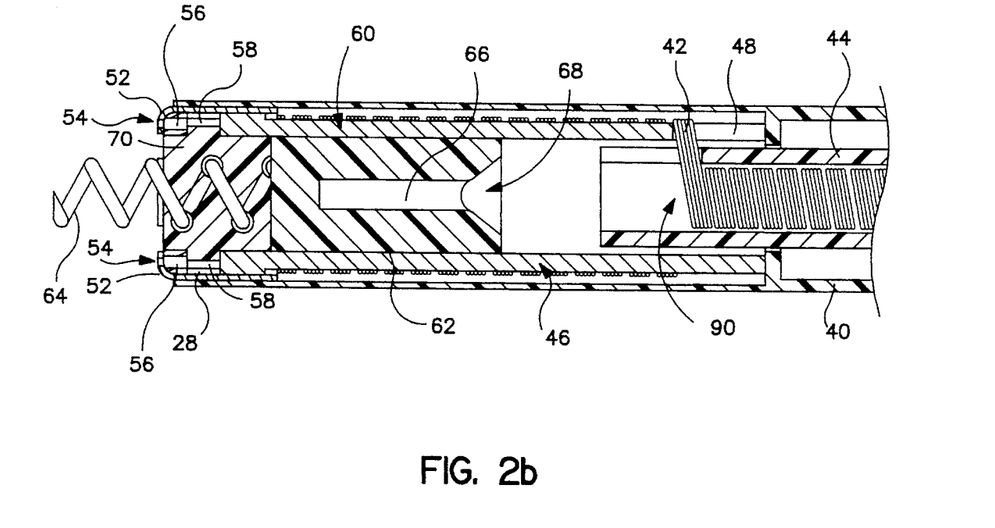

In FIG. 2a, there is shown a greatly enlarged cross-sectional side view of a distal portion of lead body 12 and electrode and fixation assembly 26. In FIG. 2b there is shown the portion of FIG. 2a contained within dashed line 2b, and in FIG. 2c there is shown the portion of FIG. 2a contained within dashed line 2c, both even further enlarged for the sake of clarity.

Figure 2C:
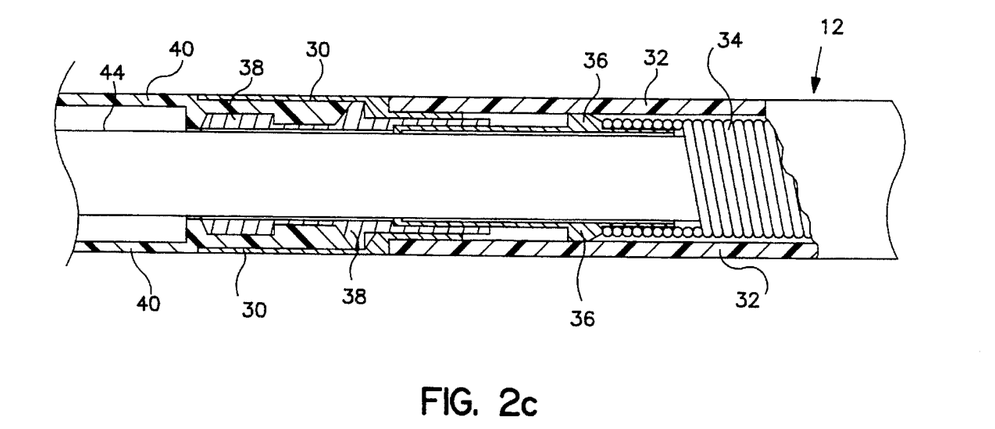

As shown in FIGS. 2a and 2c, lead body 12 has an outer flexible insulative sheath 32 made of silicone rubber, polyurethane, or the like. Outer insulative sheath 32 covers first coiled conductor 34. Conductor 34 extends along through lead body 12 and terminates at its distal end where it is electrically coupled, for example by spot or laser welding, to a crimp sleeve 36 made of stainless steel or the like. Crimp sleeve 36, in turn, is in electrical connection with a sleeve 38 which is similarly made of stainless steel or the like. Sleeve 38 is engaged within and in electrical contact with substantially cylindrical ring electrode 30, which is preferably made of a 90/10 platinum/iridium alloy.

Partially engaged between ring electrode 30 and sleeve 38 is a tip/ring spacer 40, which is preferably made of silicone rubber. In addition to establishing a predetermined distance between ring electrode 30 and tip electrode 28, tip/ring spacer 40 functions to define a substantially cylindrical chamber in which the remaining components are disposed as well as to define the outer surface of electrode and fixation assembly 26. In the disclosed embodiment, tip/ring spacer 40 has dimensions such that a constant lead body diameter is maintained between tip electrode 28 and ring electrode 30.

Figure 4:
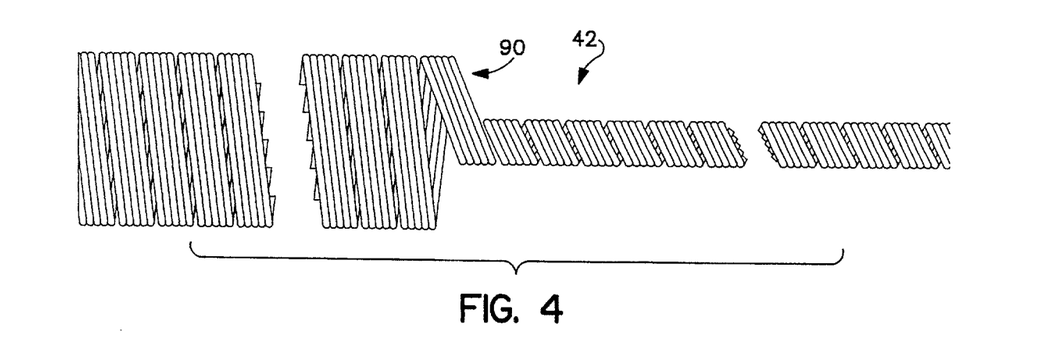
FIG. 4 is a greatly enlarged side view of a coiled conductor within the lead of FIG. 1.

Extending along the length of lead body 12 through crimp sleeve 36, sleeve 38, ring electrode 30, and tip/ring spacer 40 is a second coiled conductor 42, which is insulated from outer coiled conductor 34 by inner insulative sheath 44 which, like outer sheath 32 is made of silicone rubber, polyurethane, or the like. Inner conductor 42 terminates at a substantially cylindrical helix sleeve 46. In the presently preferred embodiment, helix sleeve 46 is made of machined polysulfone, and is provided with a rectangular slot 48 which allows the diameter of the coil defined by inner conductor 42 to increase at a "dog-leg" point designated generally as 90 in FIGS. 2a and 2b. Distally from "dog-leg" point 90, inner conductor 42 coils around the outer surface of helix sleeve 46 toward the distal end of helix sleeve 46, and is electrically coupled, e.g., by spot or laser welding, to tip electrode 28. The configuration of inner conductor 42 and "dog-leg" point 90 are best seen in FIG. 4, which shows conductor 42 in isolation.

Figure 3A:
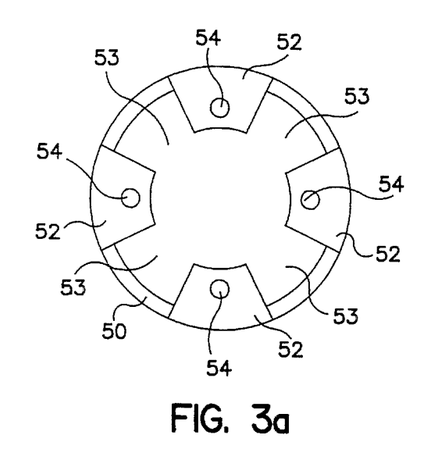
Figure 3B:
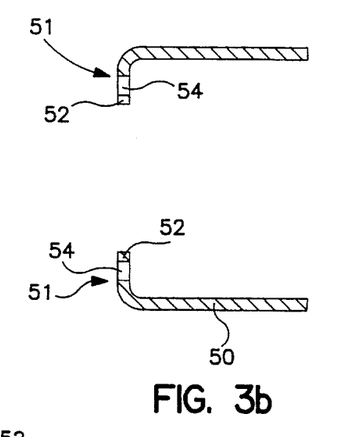

At its distal end, inner conductor 42 is electrically coupled, via spot or laser welding or the like, to tip electrode 28, shown in FIGS. 3a and 3b, respectively. Tip electrode 28 comprises a substantially cylindrical portion 50 and a forward-oriented oriented face portion comprising a substantially annular section 51. Annular section 51 has a segmented pattern of forward-facing tabs 52 arranged radially about the lead body axis and separated from one another by a segmented pattern of spaces 53. Tabs 52 each have a through-hole 54 therein, where through-holes 54 function as steroid-elution ports, as will be hereinafter described.

In accordance with the presently disclosed embodiment of the invention, a porous structure (not shown) is sintered onto tabs 52 and over through-holes 54. The porous structure may be made by mixing a conductive material and a binder to form a conductive slurry mixture. Next this slurry may be deposited onto tabs 52 and sintered. Once sintered the porous structure is then preferably electroplated with a material to provide a relatively high microscopic surface area, such as platinum black in the preferred embodiment. Electroplating may be accomplished in any manner suitable.

In the preferred embodiment, platinizing may be accomplished by immersing tip electrode, as cathode, in a platinizing solution, such as one consisting of three percent (3%) platinum chloride dissolved in 0.025 percent lead acetate solution. An anode of inert metal may then be placed into the platinizing solution and a sufficient current passed through the cell so that small bubbles are visible. This process should be continued until a layer of platinum black is deposited over the entire electrode. This process, cleaning and platinizing, produces an electrode having a platinum black surface coating which is sufficiently durable to permit it to be implanted within a body. The porosity, together with the platinum black coating is intended to reduce source impedance and polarization, as is well known in the art.

Except for the sintered distal faces of tabs 52, the remainder of tip electrode 28 is preferably insulated, thereby increasing the electrode pacing impedance by minimizing the exposed macroscopic surface area thereof. Those of ordinary skill in the art will appreciate that the macroscopic surface area is further minimized as a result of radially-oriented spaces 53 of the forward-facing, substantially annular portion 51 of electrode 28, since the presence of spaces 53 leaves only tabs 52 exposed to make electrical contact with endocardial tissue.

Although tip electrode 28 is segmented through four forward-facing radially-oriented tabs 52 (and a corresponding number of intervening spaces 53) it is contemplated electrode 28 may alternatively have more or fewer tabs 52 and spaces 53.

Figure 3C:
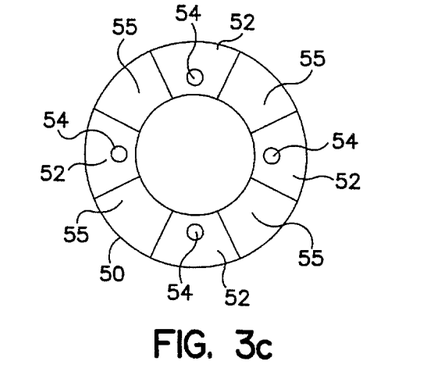
FIG. 3c is a front view of an alternate embodiment of a distal tip electrode.

In an alternative embodiment depicted in FIG. 3c, no radially-oriented space sections 53 are provided; instead, annular portion 51, although intact, is coated in radially-oriented sections with an insulative material 55, such that annular section 51 effectively comprises alternating radially-oriented conductive and non-conductive segments.

Referring again to FIGS. 2a and 2b, tip/ring spacer 40 covers cylindrical body portion 50 of tip electrode 28, and is preferably secured thereto with silicone medical adhesive. Disposed within tip electrode 28, directly behind annular portion 51, is a washer-like polysulfone electrode shim 56 having holes therein which, in the presently disclosed embodiment of the invention, align with holes 54 in tabs 52 of tip electrode 28, previously described with reference to FIG. 3a. Directly behind electrode shim 56 is an annular space occupied by a similarly annular steroid monolithic controlled release device (MCRD) 58. Holes 54 and the corresponding holes in electrode shim 56, along with the porous sintered coating on tabs 52, allow steroid to elute into the tissue proximate to the distal end of lead 10.

In an alternative embodiment of the invention, it is contemplated that tabs 52 may not be provided with steroid-elution through-holes 54. Instead, steroid elution could be accomplished though electrode shim 56 in the regions thereof which align with spaces 53 in annular section 51 of electrode 28. That is, electrode shim may itself be porous, at least in the regions which align with spaces 53, such that no steroid-elution ports 54 would be required in tabs 52.

Figure 5:
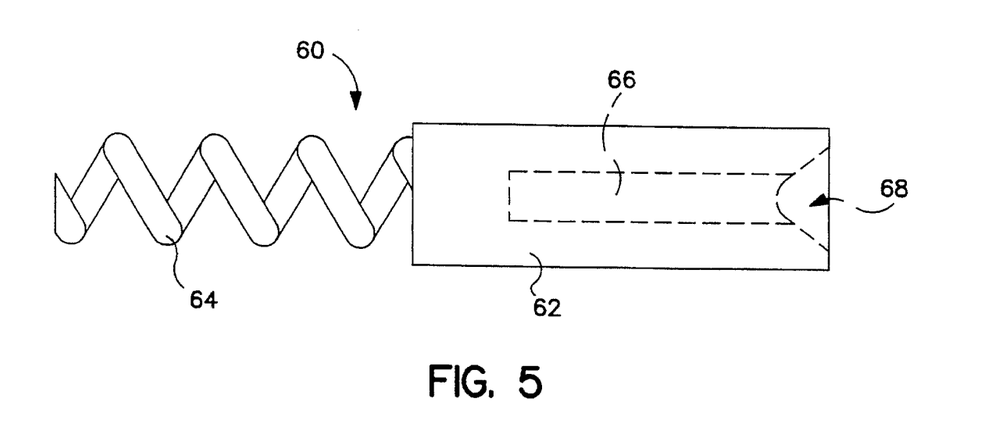

Helix assembly 60 is slidably disposed, in a piston-like fashion, in the cylindrical interior of helix sleeve 46. A greatly enlarged side view of helix assembly 60 is shown in FIG. 5. Helix assembly 60 comprises a stylet socket portion 62, which is preferably made of hard plastic, and a sharpened helix 64, the base of which may be molded into stylet socket 62 and which extends axially outward from stylet socket 62. Helix 64 is preferably made of a platinum/iridium alloy. As shown in FIGS. 2a, 2b, and 5, stylet socket 62 has an axially-oriented rectangular slot 66 formed therein, preferably having a flared opening 68 corresponding to screw-driver tip of a stylet, described below.

Figure 6A:
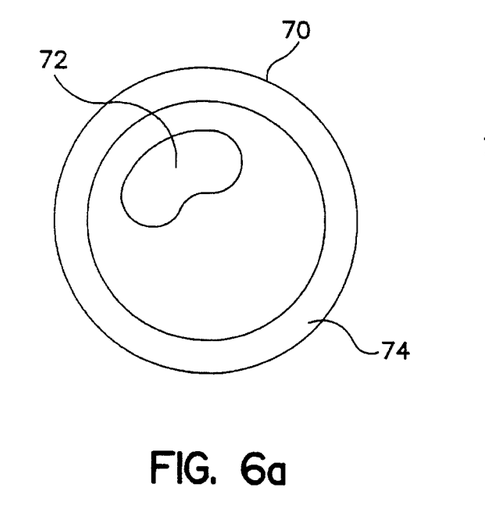
Figure 6B:
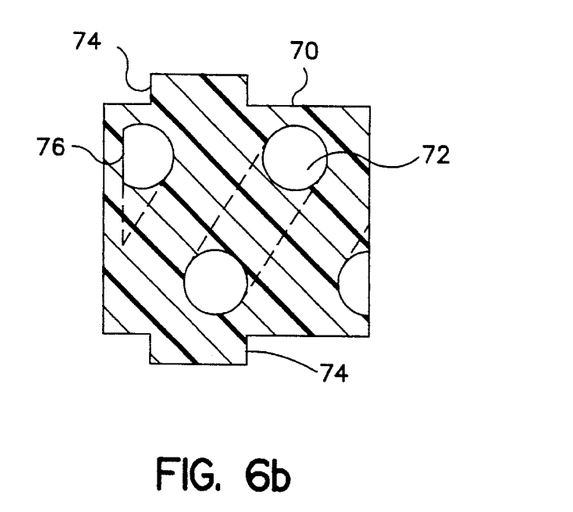

Helix assembly 60 is secured within helix sleeve 46 by means of a substantially cylindrical helix seal 70, seen in FIGS. 6a and 6b, which is made of molded silicone rubber. Helix seal 70 is provided with a helical lumen or channel 72 extending from front to back, through which helix 64 is able to pass, as depicted in FIGS. 2a and 2b. Helix seal 70 is further provided with a flared portion 74 around its circumference to secure seal 70 between electrode shim 56 and helix sleeve 46. When so secured, the front (distal) end of helix seal 70 defines a substantially circular, non-conductive central portion in the face of tip electrode 28.

Referring to FIG. 6b, helical lumen 72 in helix seal 70 is sealed at point 76. When helix 64 is screwed into helix seal 70 from the back, helix seal 70 guides helix 64 to advance forward, such that the pointed tip of helix 64 pierces point 76 of lumen 72. When helix 64 is screwed back out, the resiliency of silicone rubber seal 70 is such that lumen 72 effectively seals itself. This self-sealing arrangement is believed to be advantageous in that it tends to prevent body fluids from entering electrode and fixation assembly 26.

The active fixation mechanism is actuated by means of a stylet 24 whose distal end is flattened into a slotted head or screw-driver type of configuration. A greatly enlarged side view of stylet 24 in FIG. 7a, and an even more enlarged distal end view of stylet 24 is shown in FIG. 7b. Stylet 24 is preferably made of stainless steel, and preferably has a knurled plastic knob 25 disposed on its proximal end to facilitate manipulation.

Figure 7A:
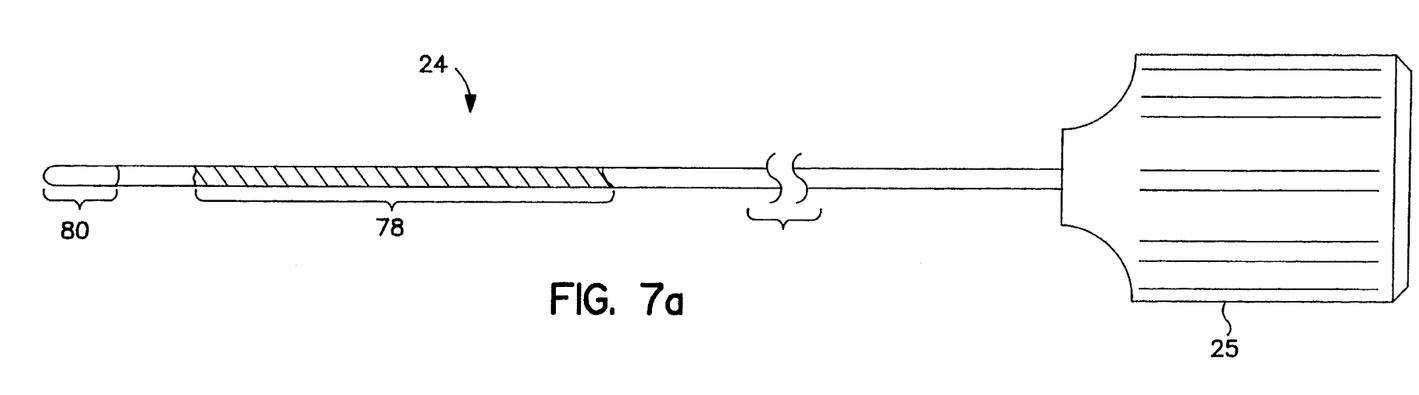
FIGS. 7a and 7b are greatly enlarged side and distal end views, respectively, of a stylet used in conjunction with the lead from FIG. 1.
Figure 7B:
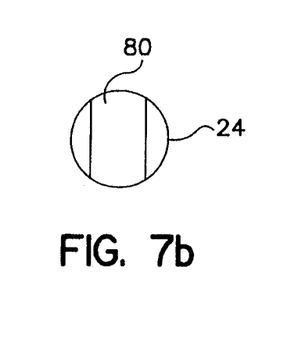

Distal section 78 of stylet 24 is made of coiled torque cable, as best seen in FIG. 7a. Atrial leads often have a preformed "J" shape at their distal end, to facilitate implantation and maintain the lead in good electrical contact with a trial tissue. As a result of this "J" shape, it is often difficult to rotate a conventional curved stylet to advance helix assembly 60 without movement of the lead tip, causing the electrode to be dislodged. Torque cable section 78 of stylet 24, in contrast, permits the transmission of torque to the helix through such a curved lead. For ventricular applications, torque cable section 78 of stylet 24 may not be necessary.

As best seen in FIG. 7b distal end 80 of stylet 24 is flattened to form a slotted-head or screw-driver configuration such that it can be received within rectangular slot 66 in helix sleeve 46. This configuration enables torque generated through twisting stylet 24 can be used to rotate helix assembly 60. Since helix seal 70 is rigidly secured within electrode and fixation assembly 26, any rotation of helix assembly 60 will cause helix 64 to travel axially forward or backward, depending upon the direction of rotation of stylet 24. In the most retracted position of helix assembly 60 (a position not shown in the FIGS.) the tip of helix 64 is disposed within helix seal 70, i.e. proximal with respect to sealed portion 76 of helix seal 70. Helix assembly 60 is shown in FIGS. 2a and 2b in its most extended position, wherein stylet socket 62 is pushed distally up against helix seal 70. Further details concerning the construction and operation of such a stylet may be found in the co-pending application of James T. Gates and Kenneth B. Stokes entitled "MEDICAL ELECTRICAL LEAD SYSTEM HAVING A TORQUE TRANSFER STYLET" filed this same day and assigned to the assignee of the present invention.

Transvenous implantation of lead 10 may be accomplished using conventional lead introduction techniques.

During the implantation procedure, stylet 24 is used to provide stiffness to lead body 12, facilitating manipulation of lead 10 through the patient's venous system. Helix assembly 60 is maintained in its most retracted position until the distal end of electrode and fixation assembly is brought into contact with the desired endocardial stimulation site. Since helix assembly 60 is contained completely within the electrode and fixation assembly, it is prevented from damaging tissue as lead 10 is advanced through the venous system.

Once the desired electrode positioning is achieved, stylet 24 is rotated in the appropriate direction to cause helix 64 to advance through helical channel 72 within helix seal 70, eventually piercing sealed portion 76 at the distal end of helical channel 72. Continued rotation of helix 64 will cause further advancement, so that helix 64 pierces and engages the endocardial tissue. In this way, electrode and fixation assembly 26, and in particular, tip electrode 28, is secured in contact with the desired stimulation site. The porous sintered coating on tabs 52 of electrode 28 allows steroid from MCRD 58 to elute from the lead at the location of the lead/tissue interface. Thus, the full benefits associated with steroid elution, well documented in the prior art, are realized, and secure fixation of the lead at the stimulation site is achieved.

A further advantage of the present invention is that the fixation mechanism of lead 10 can be released, without significant damage to the cardiac tissue, by simply rotating stylet 24 in the opposite direction. Such retraction of helix 64 may be desired, for example, if it is necessary to relocate the lead.

A still further advantage of the present invention is that it permits the electrode to contact heart tissue without first inserting the helix. Thus the optimal site for stimulating may be selected without imposing trauma to the heart tissue.

Although a specific embodiment of the invention has been disclosed, this is done for the purposes of illustration and is not intended to be limiting with regard to the scope of the invention. It is contemplated that various substitutions, alterations, and/or modifications, including but not limited to those specifically discussed herein, may be made to the disclosed embodiment of the invention without departing from the spirit and scope of the invention as defined in the appended claims, which follow.

What is claimed is:

1. An electrode assembly comprising a substantially annular electrode face having a plurality of alternating conductive and non-conductive radially-oriented segments disposed perpendicularly about a substantially circular, non-conductive central portion, the electrode face being disposed upon a distal end of the electrode assembly wherein at least one of the segments has at least one drug-elution port formed therein, and wherein the electrode assembly has a monolithic controlled release device disposed proximal to the annular face.

2. An electrode assembly in accordance with claim 1, wherein the at least one drug-elution port is disposed in at least one of the conductive segments of the annular face.

3. An electrode assembly in accordance with claim 2, wherein the conductive segments on the annular face have a porous sintered coating disposed thereon, and wherein the drug-elution port is located proximal to the porous sintered coating.

4. An electrode assembly in accordance with claim 1, further comprising:

a fixation helix rotatably disposed within the substantially circular, non-conductive central portion of the electrode;

a helix seal, rigidly disposed within the substantially circular, non-conductive central portion, the helix seal having a helical channel such that upon rotation of the fixation helix in a first direction, the helix seal guides the helix to advance distally out from the substantially circular central portion, and such that upon rotation of the fixation helix in a second direction, the helix seal guides the helix to retract proximally into the substantially circular central portion.

5. An electrode assembly in accordance with claim 4, further comprising a stylet socket coupled to the fixation helix, the stylet socket having a configuration for receiving a stylet tip therein for remote rotation of the helix.

6. A medical lead comprising:

a lead body, the lead body having a first coiled conductor;

a terminal assembly positioned on a proximal end of the lead body; and an electrode assembly disposed at a distal end of the lead body, the electrode assembly comprising a substantially annular electrode face having a plurality of alternating conductive and non-conductive radially-oriented segments disposed about a substantially circular, non-conductive central portion, said plurality of alternating conductive radially-oriented segments coupled to the first coiled conductor.

7. A lead in accordance with claim 7, wherein the annular electrode face of the electrode assembly has at least one drug-elution port formed therein, and wherein the lead further includes a monolithic controlled release device disposed proximal to the annular face of the electrode.

8. A lead in accordance with claim 7, wherein the at least one drug-elution port is disposed in at least one of the conductive segments of the annular face of the electrode.

9. A lead in accordance with claim 8, wherein the conductive segments on the annular electrode face have a platinized, porous sintered coating disposed thereon and wherein the drug elution port is located proximal to the platinized, porous sintered coating.

10. A lead in accordance with claim 6, further comprising:

a fixation helix, rotatably disposed proximal to the substantially circular, non-conductive central portion of the electrode;

a helix seal, rigidly disposed within the substantially circular, non-conductive central portion of the electrode face, the helix seal having a helical channel therein for receiving at least one turn of the fixation helix, such that upon rotation of the fixation helix in a first direction, the helix seal guides the helix to advance distally out from the substantially circular central portion, and upon rotation of the fixation helix in a second direction, the helix seal guides the helix to retract proximally into the substantially circular central portion.

11. A lead in accordance with claim 10, further comprising a stylet socket, rigidly coupled to the fixation helix, the stylet socket having a configuration for receiving a stylet tip therein for remote rotation of the helix.

12. A lead in accordance with claim 11, wherein the lead body has a longitudinal lumen extending between proximal and the distal end, adapted to receive a stylet having a slotted-head tip therein and facilitate advancement of the slotted-head tip to engage the stylet socket.

13. A medical lead comprising:

a lead body having a first coiled conductor and a second coiled conductor, the lead body having a terminal assembly positioned on a proximal end of the lead body;

an electrode assembly disposed at a distal end of the lead body, the electrode assembly comprising a cylindrical tip electrode having a plurality of conductive radially-oriented segments disposed perpendicularly about a distal end of the cylindrical tip electrode;

a helix seal positioned within the tip electrode, the helix seal having a helical path therethrough; and a helix assembly disposed within the lead body, the helix assembly having a socket portion and a helix extending from the socket portion through at least a portion of the helical path through the helix seal wherein a rotation of the socket portion in a first direction causes the helix to move in a first direction coaxial with the lead body and rotation of the socket portion in a second direction causes the helix to move in a second direction coaxial with the lead body.

14. A lead in accordance with claim 13, wherein at least one of the plurality of conductive radially-oriented segments disposed perpendicularly about the distal end of the tip electrode has a drug-elution port formed therein, and wherein the lead further includes a monolithic controlled release device disposed proximal to the annular face of the electrode.

15. A lead in accordance with claim 13, wherein at least one of the plurality of conductive radially-oriented segments disposed perpendicularly about the distal end of the tip electrode have a platinized, porous sintered coating disposed thereon.

* * * * *